United States Patent [19]

Drennan

[11] Patent Number: 5,433,695
[45] Date of Patent: Jul. 18, 1995

[54] FOOT PIECE FOR WALKING CAST

[75] Inventor: Denis B. Drennan, Evanston, Ill.

[73] Assignee: DM Systems, Inc., Evanston, Ill.

[21] Appl. No.: 239,347

[22] Filed: May 6, 1994

[51] Int. Cl.⁶ .................................................. A61F 5/00
[52] U.S. Cl. ........................................ 602/10; 36/15; 36/19.5; 602/11; 602/23
[58] Field of Search ............. 602/5, 10, 11, 23, 27–29; 128/882; 36/15, 100, 101, 19.5

[56] References Cited

U.S. PATENT DOCUMENTS

| | | |
|---|---|---|
| 2,189,053 | 2/1940 | Bryant . |
| 2,264,570 | 12/1941 | Holden . |
| 2,392,735 | 1/1946 | Hahn . |
| 2,490,849 | 9/1949 | Gersh et al. . |
| 2,526,205 | 10/1950 | Doerschler . |
| 2,762,367 | 9/1956 | Rubin . |
| 2,888,919 | 6/1959 | Unkauf . |
| 3,481,332 | 12/1969 | Arnold . |
| 3,613,674 | 10/1971 | Volz . |
| 3,693,269 | 9/1972 | Guarrera .......................... 36/15 |
| 4,641,639 | 2/1987 | Padilla . |
| 4,821,432 | 4/1989 | Reiber ............................ 36/110 |
| 4,966,135 | 10/1990 | Renfrew . |
| 5,092,321 | 3/1992 | Spademan ...................... 602/27 |

FOREIGN PATENT DOCUMENTS 885599 8/1953 Germany .
673716 6/1952 United Kingdom .

OTHER PUBLICATIONS

Richards Mfg. Co. Catalog, 1966, p. 40.

Primary Examiner—Linda C. M. Dvorak
Attorney, Agent, or Firm—Mason, Kolehmainen, Rathburn & Wyss

[57] ABSTRACT

A foot piece of elastomeric material is provided for converting a new leg and foot cast and/or an already existing leg and foot cast into a walking cast by permanent attachment of the foot piece to a sole surface of the cast. The foot piece has an upper surface generally conforming to the shape and size of the sole surface of the cast and a layer of uncured adhesive material is provided on the upper surface. The adhesive layer is protected against curing or setting until ready for use by a thin layer of air-impervious film which is stripped or peeled away to initiate curing when the foot piece is pressed or forced against the sole surface of the cast and is held until the adhesive material cures or sets to provide a permanent adhesive attachment of the foot piece on the cast for converting the cast for walking.

12 Claims, 2 Drawing Sheets

U.S. Patent  July 18, 1995  Sheet 1 of 2  5,433,695
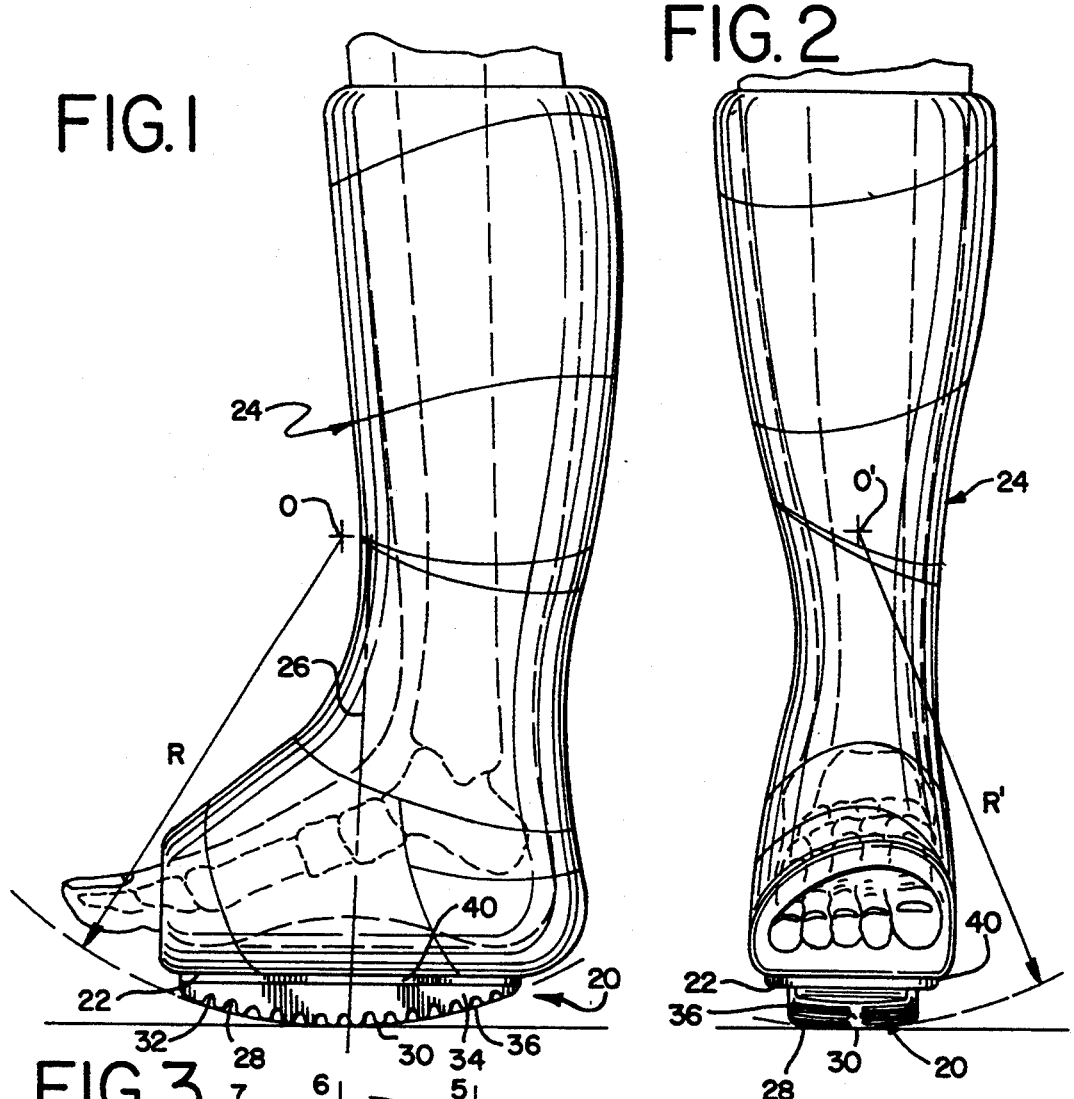
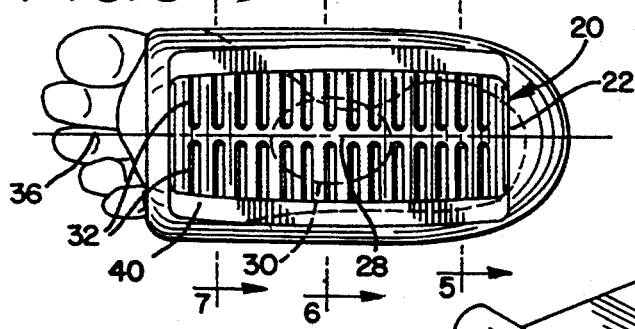
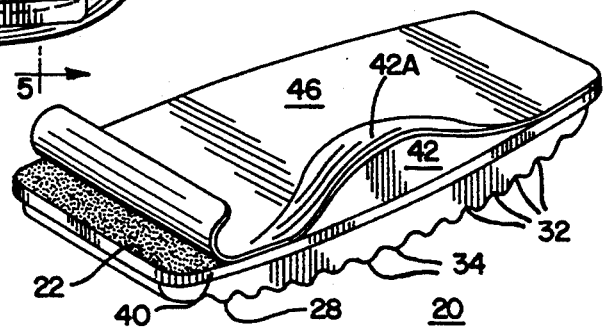

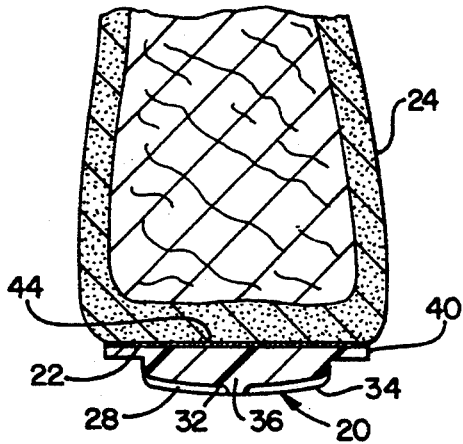
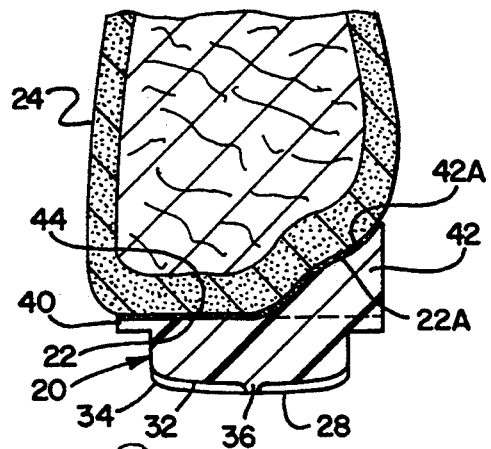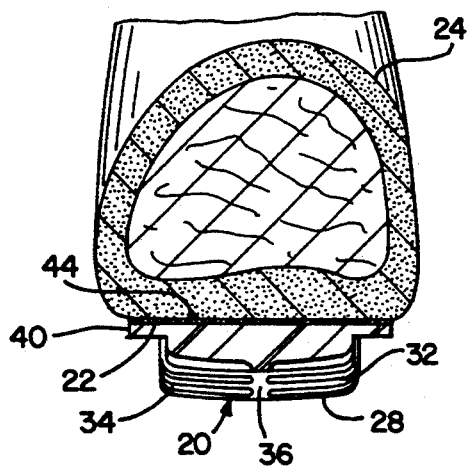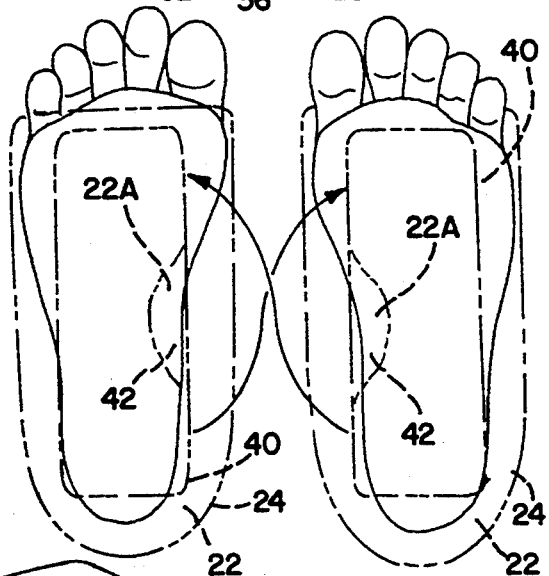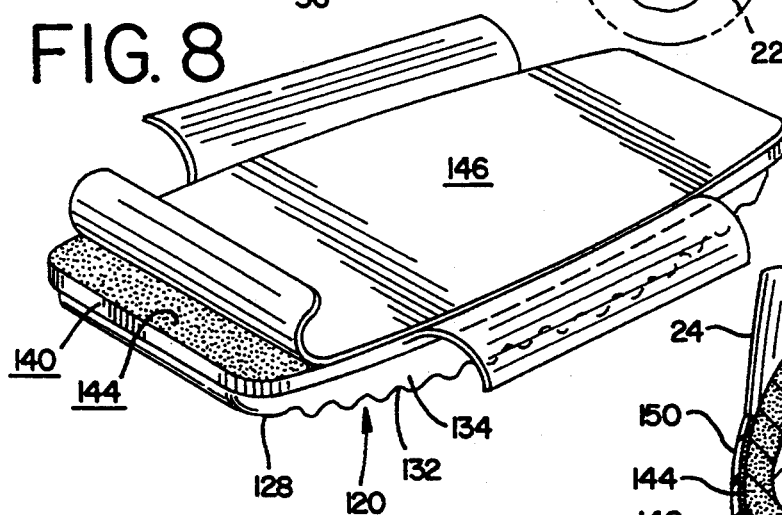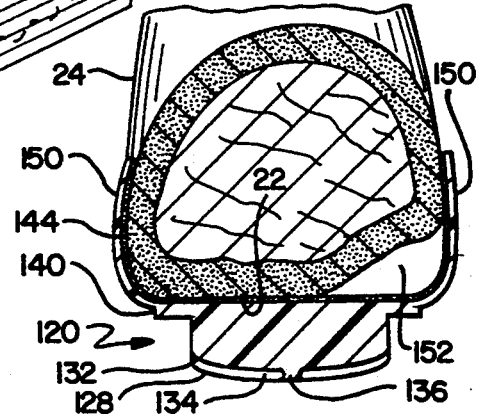

FOOT PIECE FOR WALKING CAST

BACKGROUND OF THE INVENTION 1. Field of the Invention

The present invention relates to a new and improved foot piece of elastomeric material used for converting a leg and foot cast into a walking cast by permanent attachment of the foot piece to a sole surface of the cast. Initially when a plaster of Paris or fiberglass cast is applied for an injury to the foot or leg of a patient it is not always desirable that the patient be permitted to walk immediately after the cast is in place. Many times a period of from one to six weeks may transpire before the patient would be permitted to walk on the affected leg. Also, it is desirable in some cases that, the cast already in place not be removed and replaced but merely converted into a cast suitable for walking pressure when the patient has healed enough and is ready to walk.

The present invention is designed to provide a simple, economical and effective means for converting an already existing leg and foot cast which may have been in place for several weeks into a cast suitable for permitting the patient to walk with little danger of adding additional stress or trauma to the patient's leg and foot during walking. 2. Background of the Prior Art U.S. Pat. No. 2,189,053 to Bryant discloses an ambulatory splint having a U-shaped stirrup which must be molded into the original cast when applied so that later on, a foot frame can be attached to the bight portion of the stirrup with screws.

Similarly, in U.S. Pat. No. 2,264,570 to Holden, side members and extension members are impressed into the plaster of Paris along with a bight member below the patient's foot while the cast material is still soft and later on, a foot assembly is attached to the embedded member.

U.S. Pat. No. 2,392,735 to Hahn discloses a walking device utilizing a metal U-shaped frame with side members joined to a transverse bottom member and at the upper ends the side members are provided with curved sections which along with guide members are wrapped within the plaster of Paris impregnated gauze as the cast is applied.

The Gersh et al. U.S. Pat. No. 2,480,849 discloses a surgical cast having a support with leg straps embedded in the cast and a bight of a U-shaped element is attached to exposed lower end portions of the straps to support a walking pad.

U.S. Pat. No. 2,526,205 to Doerschler discloses a walker wherein a foot piece is secured to the lower end of a cast by means of a plaster of Paris impregnated bandage wrapped around the foot and leg and passed through a slot in the foot piece while the plaster of Paris is still wet or soft. Similarly, a plurality of U-shaped wires are also passed through the foot piece and up into the soft plaster of Paris which hardens to secure the foot piece in place.

U.S. Pat. No. 2,762,367 to Rubin discloses a walking aid for a splinted human leg wherein a walking stirrup is embedded in the cast with a cradle beneath the patient's foot and subsequently a walking aid is secured thereto by means of bands extending around the patient's foot.

U.S. Pat. No. 2,888,919 to Unkauf discloses a walking heel adapted to be implanted within a plaster of Paris cast to support the heel of the patient during walking or standing.

U.S. Pat. No. 3,481,332 to Arnold discloses a walker and cast reinforcement wherein a rotatable ground engaging cleat is mounted on the lower side of the cast having a mounting element secured in the cast.

U.S. Pat. No. 3,613,674 to Volz discloses a foot and leg walking cast having a rocker-shaped base with a rounded, ground engaging base and thin side flaps of flexible material which are wrapped around the cast and secured in place with plaster of Paris impregnated gauze strips.

U.S. Pat. No. 4,641,639 to Padilla discloses an ambulatory brace assembly including an open faced cast formed of rigid material and lined with soft material wherein a pair of retainers are at the front of the leg on the open side of the cast and a U-shaped support having legs and a bight is provided securable by flexible straps having "Velcro" R type hook and loop fasteners thereon and wrapped around the cast at two different elevations.

Renfrew U.S. Pat. No. 4,966,135 discloses an orthopedic cast cover for protection of a casted limb from water, etc.

British Patent Specification No. 673,716 discloses a walking plaster appliance for use by orthopedic patients having a relatively thick sole of rubber and side flaps which are laced into place around the cast.

German Pat. No. 885,599 discloses a loop of flexible material having a thickened lower sole portion for walking wherein the toe and front portion of the patient's casted foot is inserted within the loop.

Rubber walking heels for use with leg and foot casts are disclosed at page 40 of Richards Mfg. Co. catalog dated 1966 and received in Group 33, May 9, 1966.

OBJECTS OF THE INVENTION

It is an object of the present invention to provide a new and improved foot piece adapted for adhesive permanent attachment to an already existing leg and foot cast formed of plaster of Paris or other plastic material.

It is another object of the present invention to provide a new and improved footpiece for attachment to a new fiberglass leg and foot cast and/or an already existing leg and foot cast formed of plaster of Paris or other plastic material.

It is another object of the present invention to provide a new and improved cast and foot piece combination wherein the foot piece can be secured to the cast at any time yet does not require any braces, stirrups or other elements to be embedded in the cast while it is initially applied.

Yet another object of the present invention is to provide a new and improved foot piece in accordance with the present invention which can be utilized with either foot of a patient and provide ample support therefor yet without requiring special attachment devices embedded in the original cast.

Still another object of the present invention is to provide a new and improved foot piece of the character described wherein permanent attachment of the foot piece to the underside of a cast is achieved by use of an uncured adhesive layer on an upper surface of the foot piece, which adhesive layer is activated to cure by removal of a thin air obscuring film and then moving the adhesive layer into contact with a sole surface of the cast.

Still another object of the present invention is to provide a new and improved foot piece of the character described which provides arch support for the patient and yet does not require a completely flat sole surface for the cast.

Yet another object of the present invention is to provide a universal foot piece which can be utilized with patients having different foot sizes.

BRIEF SUMMARY OF THE PRESENT INVENTION

The foregoing and other objects and advantages of the present invention are accomplished in a new and improved foot piece formed of elastomeric material and especially adapted for converting an already existing leg and foot cast formed of plaster of Paris or other plastic material into a walking cast by permanent attachment of the foot piece to a sole surface of the existing cast. A new and improved foot piece has a relatively flat upper surface generally conforming to the shape and size of a sole surface of an already existing cast and a layer of uncured pressure-sensitive adhesive material is provided on the upper surface of the foot piece and the adhesive layer is protected against damage and contamination by a thin layer of air-impervious plastic film. When a foot piece is ready to be attached onto an existing cast, the thin film is peeled away, and the foot piece is then forced and pressed against the sole surface of the cast, thus initiating curing of the adhesive material. Thereafter, permanent adhesive attachment between the old cast and the new foot piece is attained so that the existing leg and foot cast becomes a cast suitable for walking.

A foot piece in accordance with the present invention can be utilized for either a right or left foot and in either case provides good arch support. In addition, standardization of sizes can be provided so that a large number of different sizes need not be stored in advance of anticipated use. For example, foot pieces can be utilized to cover patients ranging from children of tender years up to full grown adults with very large feet. Moreover, no differentiation need be provided between male and female patients with respect to the foot piece sizes or shape.

BRIEF DESCRIPTION OF THE DRAWINGS

For a better understanding of the present invention, reference should be taken to the following detailed description taken in conjunction with the drawings, in which:

FIG. 1 is a side elevational view of a leg and foot cast on a patient with a foot piece in accordance with the present invention secured permanently in place thereon;

FIG. 2 is a front elevational view of the cast and foot piece of FIG. 1;

FIG. 3 is a bottom view of the cast and foot piece of FIG. 1;

FIG. 4 is a perspective view of the foot piece before attachment to the cast;

FIG. 5 is a fragmentary transverse cross-section taken substantially along lines 5—5 of FIG. 3;

FIG. 6 is another transverse cross-sectional fragmentary transverse cross-sectional view taken substantially along lines 6—6 of FIG. 3;

FIG. 7 is a fragmentary transverse cross-sectional view taken substantially along lines 7—7 of FIG. 3;

FIG. 8 is a perspective view of another embodiment of a foot piece in accordance with the present invention;

FIG. 9 is a transverse cross-sectional view similar to that shown in FIG. 6 with the foot piece of FIG. 8 in place on a leg cast of a patient; and FIG. 10 is an animated drawing showing the feet of a patient and a foot piece in accordance with the present invention which can be swapped end to end to be utilized for either a left foot or a right foot as shown.

DETAILED DESCRIPTION OF PREFERRED EMBODIMENTS OF THE INVENTION

Referring now more particularly to the drawings, in FIGS. 1–8 is illustrated a new and improved elastomeric foot piece 20 especially designed and adapted for permanent adhesive attachment to a sole surface 22 of a new fiberglass leg and foot cast and/or an already existing leg and foot cast 24 to convert the same into a walking cast.

In general, leg and foot casts are employed to immobilize fractures of bones, sprains or strains in the foot and leg of a patient. When a cast is initially applied, oftentimes it is not desirable that the patient walk on the casted foot until some progress in an initial healing process has taken place. This initial healing process may take a day or two up to a number of weeks and during this period a ground or floor engaging protuberance on a cast is inconvenient, heavy, cumbersome and unclean, especially when the patient is reclining or asleep and foot soil is inadvertently carried on the foot piece to the bed sheets or the like.

It is desirable to be able to convert an already existing foot and leg cast into a walking cast whenever the patient is ready to walk without the requirement of initially embedding fasteners, rods, straps, stirrups, blocks, etc. in the cast when originally applied to the patient in the anticipation of a later attachment of a ground engaging foot piece.

Typically, most leg and foot casts 24 are formed by wrapping a gauze strip or fiberglass roving strip around a patient's limb and foot. The wrapping strip is impregnated with wet plaster of Paris or plastic resins which then harden in place or cure to form a rigid body of the cast. Most casts are formed with a sole surface 22 that is relatively flat except for an arched portion 22A (FIGS. 6 and 10) on the inside of the foot below the metatarsal arch. In general, a longitudinal center or middle portion of a patient's metatarsal arch is located about half way between the ball of the foot and the heel and the mid point of the arch is approximately directly below the patient's anterior border along the front of the shin as graphically indicated by the line 26 in FIG. 1.

As viewed in side elevation in FIG. 1 and in FIG. 4 the foot piece 20 is symmetrical with respect to a lateral axis approximated by the section lines 6—6 in FIG. 3 and includes a ground engaging lower surface 28 which curves upwardly from a central portion in opposite directions fore and aft toward the toe and heel respectively. The curvature of the foot piece 20 may comprise an arcuate segment of a circle having a radius R from a point of origin 0 (FIG. 1) just ahead of the patient's anterior border 26.

Referring to FIG. 2, the undersurface 28 is also curved from side to side or laterally in a symmetrical fashion a radius R' about an origin O'. Because the undersurface 28 of the foot piece 20 curves upwardly in both a longitudinal sense (FIG. 1) and in a lateral sense (FIG. 2) in symmetrical fashion from a central ground engaging portion 30 (FIG. 3) of relatively small area in comparison to the total sole surface area 22 of the cast 24 there is very little chance that the foot piece 20 will be the cause of a patient tripping while walking or standing. Moreover, the undersurface 28 may be formed with two rows or sets of laterally extending, longitudinally spaced apart grooves 32 forming ribs 34 therebetween. Each groove has a blind end (FIG. 3) adjacent to but spaced from a longitudinal center portion 36 of the undersurface 28 and the blind ends of the grooves define a longitudinally extending continuous central rib or spine for the foot piece 20 extending from toe to heel.

In general, the small ground engaging area 30 on the undersurface 28 of the foot piece 20 is aligned directly below the thrust axis of the patient's weight during walking or standing on the casted leg so that little, if any, torsional, twisting or shear stress is developed which might inhibit healing of the patient's leg and foot.

It will also be noted that the foot piece 20 can be formed with a flat upper end portion 40 on the main body, and the body has a compound curved undersurface 28. Moreover, the area of flange (FIG. 3) is substantially larger than the area of the undersurface 28 in order to provide for better adhesion of the foot piece 20 to the sole surface 22 of the cast 24.

In order to better support, an arch portion of the cast 24, the foot piece 22 is provided with an arch-shaped filler 42 (FIG. 4) along one side edge of the upper end 40 and symmetrically disposed fore and aft. The arch filler 42 may be integrally molded with the upper end 40 or may be a separate element adhesively secured to a flat upper surface of the upper flange. In either case, the arch filler 42 includes an upper surface that generally conforms to the shape of a person's foot as altered and embodied by the cast 24 when applied. The arch support filler is symmetrical fore and aft from a maximum height at a mid portion longitudinally thereof and this permits, one type of foot piece 22 to be used for either the right or left foot merely by swapping the foot piece end for end as shown in FIG. 10 whereby the arch support filler is positioned on the inside edge of the foot. Except for the area covered by the upper surface 42A of the arch support filler 42, the upper surface of the foot piece 20 is substantially flat. Because the foot piece 20 is made of elastomeric material, the upper surface of the foot piece is relatively pliable to conform to the sole surface 22 of the cast 24.

In accordance with the present invention, the substantially flat portion of the upper surface of the narrow body of the foot piece 20 and upper flange 40 and the upper surface 42A of the arch support filler 42 are covered with a layer 44 of pressure-sensitive adhesive material (FIGS. 4-7). The adhesive layer 44 is covered over with a thin pliable, air-impervious plastic filler 46 (FIG. 4) which protects the adhesive material from damage or contamination until such time as the foot piece 20 is ready to be affixed to the sole surface 22 of the cast 24. The thin film 46 is peeled away as shown in FIG. 4 and the adhesive layer 44 is then exposed to the air and is pressed firmly against the sole surface 22 of the cast 24 and held for a prescribed time period until the adhesive sets and binds the foot piece to the cast. Usually, the wrapping material used for making a cast 24 even after it has been impregnated with plaster of Paris or plastic resin may not be perfectly flat and may have imperfections such as "dimples," "voids", etc. on the sole surface 22.

The upper surface of the foot piece 20 generally conforms to the sole surface 22 of the cast 20 and the adhesive material 44 tends to penetrate to some depth into the voids and imperfections in the sole surface 22 thus providing a permanent and extremely strong bond between the foot piece 20 and the cast 24 when the adhesive material has cured or set sufficiently. As an alternative, a suitable adhesive material may be provided from a separate tube or other closed container. This type of adhesive is spread to the necessary thickness on the sole surface 22 and upper surface of the foot piece 20 and the foot piece is held in place against the cast until the adhesive sets.

Referring to FIGS. 8 and 9, therein is illustrated another embodiment of the present invention comprising a foot piece 120 similar to the foot piece 20 previously described but, instead formed with an upper surface that is substantially flat over the entire extent. Reference numbers having a prefix "1" added thereto are used to identify components and parts of the foot piece 120 that are similar or identical to those of the foot piece 20.

Instead of an arch support filler 42, the foot piece 120 utilizes a pair of side flaps 150 formed of flexible woven roving material that is compatible with the wrapping material of the cast 24. The side flaps 154 are covered with an adhesive layer 144 that is exposed when the air-impervious film 146 is peeled away to start the curing process. When the adhesive sets or cures, the side flaps 150 become stiff and rigid and adhere tenaciously to the sides of the cast 24 above the sole surface 22. This arrangement leaves a void or open space 152 in the place where an arch support was provided in the prior embodiment. However, the stiffened side flaps 150 provide sufficient strength between the cast 24 and foot piece 20 and the basic cast is ample to support the patient's arch without further aid from the foot piece.

Obviously, many modifications and variations of the present invention are possible in light of the above teachings. Thus, it is to be understood that, within the scope of the appended claims, the invention may be practiced otherwise than as specifically described above.

What is claimed and desired to be secured by Letters Patent of the United States is:

1. In combination with a leg and foot cast having a sole surface with a relatively flat surface and a raised arch surface portion, a foot piece of elastomeric material for converting said leg and foot cast into a walking cast by permanent attachment of said foot piece to said sole surface, said foot piece having an upper surface with relatively flat surface portion and an arch surface portion generally conforming to the shape and size of said sole surface with a layer of adhesive material on said upper surface adapted to be forced against at least some of said sole surface for permanent adhesive attachment of said foot piece on said cast for walking; and said raised arch surface portion of said sole surface being positioned along one side of said sole surface of said cast between toe and heel ends of said cast; and said foot piece including an arch-shaped filler formed of elastomeric material having a cast engaging surface on said upper surface of said foot piece with a layer of adhesive material on said cast engaging surface of said filler, said adhesive layer on at least said relatively flat surface portion of said upper surface of said foot piece securing said relatively flat upper portion of said foot piece to said sole surface of said cast.

2. The combination of claim 1, wherein:

said foot piece includes an integral layer of flexible material under said adhesive layer for permitting said foot piece to better adhere to said sole surface of said cast when said foot piece is force against said sole surface for permanent attachment.

3. The combination of claim 1, wherein:
said foot piece includes a generally convex undersurface for engaging the ground, said convex undersurface symmetrically being disposed about a lateral axis spaced approximately midway between a toe end and a heel end of said foot piece, and said lateral axis being adapted to be disposed directly below a front portion of said cast, said convex undersurface curving from a lowest point below said lateral axis upwardly toward respectively said toe end and said heel end of said foot piece.

4. The combination of claim 3, wherein:
said undersurface is symmetrical with respect to a longitudinal axis centrally disposed to cross said lateral axis, said undersurface curving upwardly and outwardly in opposite directions from said longitudinal axis toward opposite sides of said foot piece.

5. The combination of claim 1, wherein:
said arch-shaped filler along one side of said foot piece generally conforms to the shape of said raised arch surface portion of said sole surface and extends longitudinally in opposite directions and is symmetrical with respect to a lateral axis at a mid-region of said foot piece.

6. The combination of claim 5, wherein:
said arch-shaped filler is adhesively secured to said relatively flat upper surface portion of said foot piece.

7. The combination of claim 6, wherein:
said layer of adhesive material is spread over an entire upper surface of said arch-shaped filler for adhesive contact with said raised arch surface portion of said cast.

8. In combination, a lower leg cast formed of flexible woven wrapping material hardened by means of plaster of Paris that has set up or a cured resinous plastic material, said cast having a sole surface extending between a toe end and a heel end of said cast, and a walking foot piece formed of resilient elastomeric material and having an upper surface portion with a flat portion and a raised arch portion adapted to be adhesively secured to said sole surface of said cast, said foot piece having a ribbed underside adapted for non-slipping contact with the ground or other surface, said underside curving downwardly and rearwardly from a forward end adjacent said toe end of said leg cast to a lowest mid-portion generally below a front portion of said cast and curving upwardly and rearwardly from said mid-portion toward a rearward end adjacent said heel end of said cast, a layer of adhesive material spread over said upper surface of said foot piece forced into contact with said sole surface of said cast for securing said foot piece permanently to said cast;
said underside of said foot piece being curved symmetrically from said mid-portion toward said forward end and said rearward end; and
said raised arch portion of said foot piece extending along one side of said foot piece and having a cast engaging surface extending upwardly of said flat portion of said upper surface, said raised arch portion having opposite half portions extending longitudinally of said mid-portion in opposite directions symmetrical thereto.

9. The combination of claim 8, wherein:
said raised arch portion of said foot piece generally conforming to an arch-shaped portion of the sole surface of said cast and symmetrical With respect to said mid-portion of said foot piece in opposite longitudinal directions.

10. The combination of claim 9, wherein:
said raised arch portion of said foot piece is adhesively joined to said arch-shaped portion of said cast with a layer of adhesive material spread over said raised arch portion.

11. The combination of claim 8, wherein:
said raised arch portion of said foot piece comprising flexible roving material adapted to be projected upwardly of said upper surface and attached to said cast, and including means for securing said roving material to said cast and stiffening said roving material to provide a rigid interconnection between said foot piece and a portion of said cast.

12. The combination of claim 11, wherein:
said raised arch portion of said foot piece comprises a sheet of flexible woven roving and said securing means comprises a resin cured on said woven roving for attaching the same to said cast and stiffening said woven roving to provide said rigid interconnection.

* * * * *